United States Patent [19]

Todd et al.

[11] Patent Number: 4,964,855
[45] Date of Patent: Oct. 23, 1990

[54] CONNECTOR WITH RECESSED NEEDLE FOR Y-TUBE, AND ASSEMBLY

[75] Inventors: Joseph J. Todd, 575 Stanford, Irvine, Calif. 92715; Earl F. Robinson, El Toro; Rex O. Bare, Irvine, both of Calif.

[73] Assignee: Joseph J. Todd, Tustin, Calif.

[21] Appl. No.: 331,245

[22] Filed: Mar. 31, 1989

[51] Int. Cl.$^5$ .............................................. A61M 39/00
[52] U.S. Cl. .................................... 604/283; 604/192; 604/288
[58] Field of Search ............... 604/280, 283, 284, 264, 604/411, 412, 905, 192

[56] References Cited

U.S. PATENT DOCUMENTS

| | | | |
|---|---|---|---|
| 4,511,359 | 4/1985 | Vaillancourt | 604/905 |
| 4,673,400 | 6/1987 | Martin | 604/283 |
| 4,810,241 | 3/1989 | Rogers | 604/905 |
| 4,834,716 | 5/1989 | Ogle, II | 604/192 |

Primary Examiner—Stephen C. Pellegrino
Attorney, Agent, or Firm—Willie Krawitz

[57] ABSTRACT

A connector is provided between an I.V. or syringe supply and a Y-tube for feeding liquid medication to a patient. The connector is an integrally formed tube having a recessed needle which is factory mounted into the distal end of the connector. At its proximal end, the tube wall of the connector defines a slot which, when rotated, will engage and form a secure lock with the sidearm portion of the Y-tube. A sterile septum is mounted within the Y-tube, and the needle penetrates the septum during use, thereby maintaining sterility. Also, since the needle is recessed, asccidental needle sticks will be reduced.

In another embodiment, the connector tube wall defines an elongate recess, and a slotted closure cap is mounted at the proximal end of the connector. The connector is fitted over the Y-tube so that the cap slot and recess coincide with the junction of the Y-tube sidearm and the Y-tube. When the cap is turned, the slot will move out of coincidence with the recess and the sidearm, causing the connector and Y-tube to lock.

14 Claims, 2 Drawing Sheets

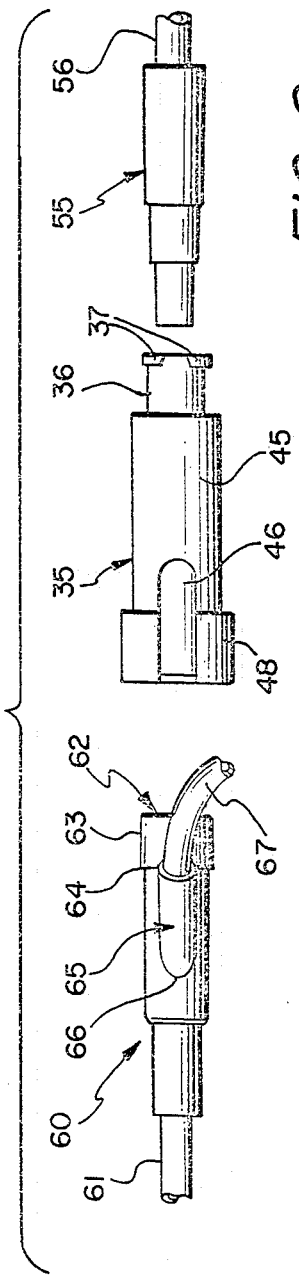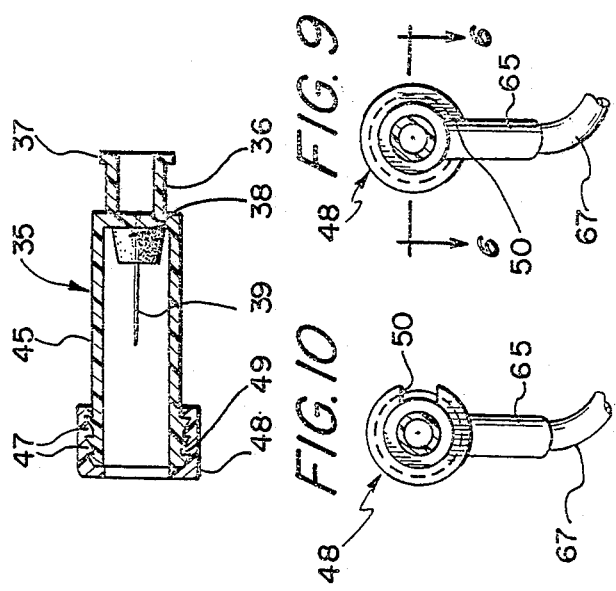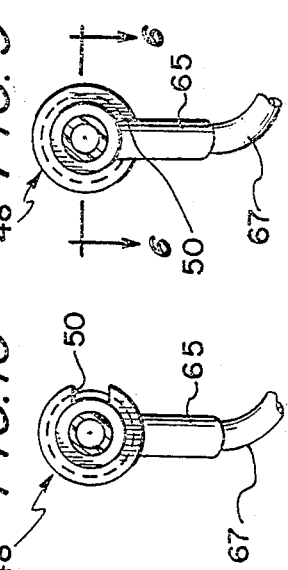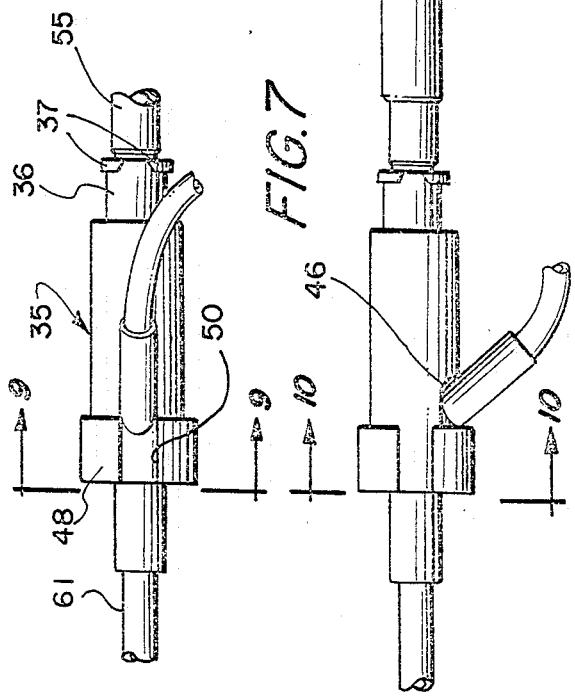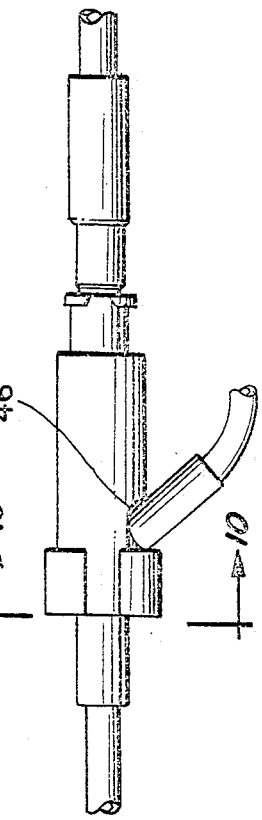

CONNECTOR WITH RECESSED NEEDLE FOR Y-TUBE, AND ASSEMBLY

BACKGROUND OF THE INVENTION:

This invention relates to a new and improved connector for use between a Y-tube and an I.V. source, syringe, and the like. The connector employs a recessed needle which reduces or eliminates accidental needle sticks, and is maintained sterile by means of a septum positioned in the Y-tube. The connectors of this invention are inexpensive, and form a secure lock with a minimum of manipulation.

Many devices are available which connect an I.V. source to the primary line for feeding medication to a patient. Generally, these devices are of the multi-purpose type, and hence are quite expensive. Since these connectors are changed frequently during the stay of a patient, their overall cost over a period of time can add considerably to the expense of a hospital. More importantly however, on many occasions, connector devices are not securely attached to a Y-connector or Y-tube which connects to the primary line. Hence, tape is used to secure these components; but the tape can be worked loose. Consequently, if the connector becomes separated from the primary line of a patient, the reult could be catastrophic, particularly if the patient is in intensive care.

Hence, a need exists for an inexpensive connector which is secure, sterile, and which can minimize or even eliminate the possibility of accidental needle sticks. Also, the connector should be easy to instal, monitor and remove, irrespective of lighting conditions. Preferably, the connector should require specific or positive manipulation to disconnect it from the primary line of the patient, rather than a disconnection by accidental handling. This would preclude random or unintentional movements by the patient resulting in the possibility of disconnecting the I.V. supply. Of course, it would be very desirable to completely eliminate the need for using adhesive tape in these connector assemblies.

THE INVENTION:

According to the invention, a connector device is provided for coupling a Y-tube on a primary I.V. feed line with a supply line from an I.V. source, syringe, and the like. The connector device is tubular shaped and has a slot or recess which, when aligned with the junction of the Y-tube sidearm, permits the coupling to slide over the Y-tube. If the connector and Y-tube are then misaligned by rotation, they will then become locked.

In one embodiment of the invention, the tubular shaped connector defines on its sidewall a slot which coincides with the Y-tube sidearm at its base, when the connector and Y-tube are fitted together. Rotation of the connector will then interlock them at the base of the sidearm.

In a second embodiment, the connector is provided with a slotted end cap, and the connector wall defines a recess. When the connector and Y-tube are initially fitted together, the recess, cap slot and sidearm base will be aligned. When the end cap is rotated, it will cause the slot to move out of alignment, and thereby lock the connector and Y-tube. In both embodiments, a disconnection of the connector and Y-tube due to random movement of the patient, or by an accidental manipulation of the device components, or by slippage is virtually eliminated.

BRIEF DESCRIPTION OF THE DRAWINGS:

FIG. 5 is an exploded, external side elevation view of another embodiment of the connector of this invention, prior to assembly with a Y-tube and luer slip;

FIG. 6 is an external side elevation view of the assembled device, prior to locking;

FIG. 7 is an external view in side elevation of the assembled device after locking;

FIG. 8 is a sectional view in side elevation of the connector;

FIG. 9 is a sectional end elevation view, taken along lines 9—9 of FIG. 6; and,

FIG. 10 is a sectional end elevation view, taken along lines 10—10 of FIG. 7.

Figure 1:
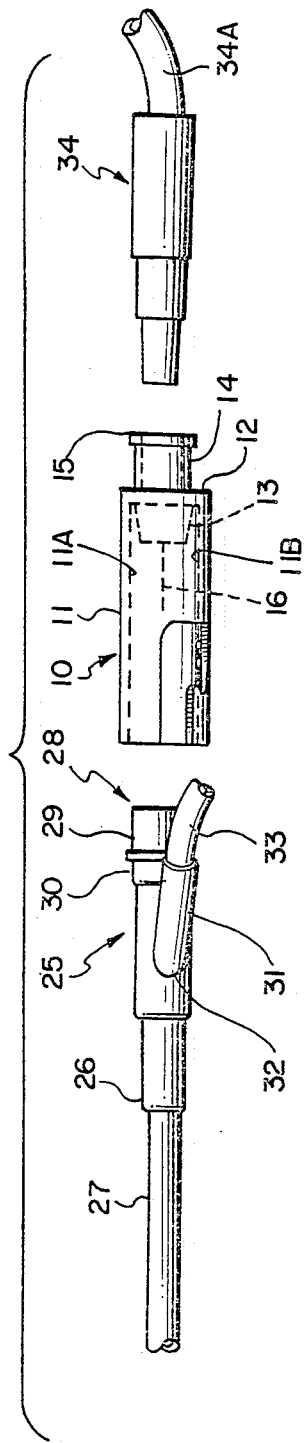
FIG. 1 is an exploded, external side elevation view of the connector of this invention prior to assembly with a Y-tube and luer lock.

DESCRIPTION OF THE PREFERRED EMBODIMENTS:

The connector 10 of this invention is shown in FIG. 1 prior to assembly, and comprises an integrally molded tubular cylinder of a resilient plastic such as polycarbonate, polypropylene, high density polyethylene, etc., which is preferably transparent or transluscent. The connector 10 provides a sidewall 11, having an exterior surface 11a and an interior surface 11b. At one end of the connector is a distal port 12 into which is formed a needle hub 13, and a fitting element 14 having locking ears 15 for connection to a corresponding luer lock. A needle 16 is factory mounted through the needle hub 13, and centrally of the tubular cylinder.

Figure 4:
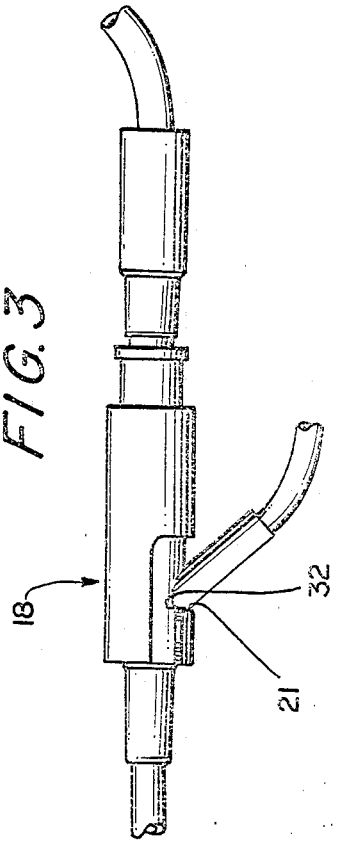
FIG. 4 is an external, perspective view of the assembled connector after locking.

As shown in FIG. 4, a cut-out or slot 17 is formed on the sidewall 11 at the proximal end 18 of the connector. The slot defines an elongate area 19, and an adjoining rounded area 20 having a rounded notch 21.

The Y-tube 25 portion of the assembly shown in FIG. 1 is a typical commercial type, of which many brands are available. The Y-tube has a proximal end 26 for fitting onto a primary I.V. line 27 which feeds I.V. fluid to a patient. The distal end 28 includes a 'piggyback' injection port 29 which fits into the connector 10. A peripheral, circular, ridge 30 is present on the exterior wall of the Y-tube and may be used for concentrically aligning the interior of the Y-tube with the connector. The Y-tube includes a sidearm 31 joined together at the base 32. Additional medication is fed to the patient via a tube 33 attached to the sidearm.

As shown in FIG. 1, a luer lock 34 or luer slip is shown for press fitting or locking into fitting element 14 of the connector. The luer lock is connected to a tube 34a which is fed from the I.V. source.

Figure 2:
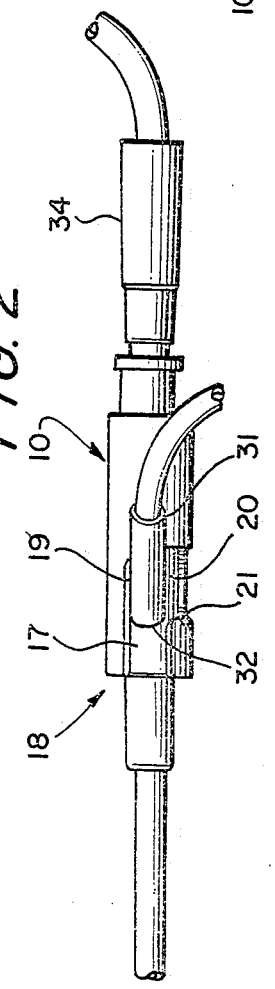
FIG. 2 is an external side elevation view of the assembled device, prior to locking.
Figure 3:
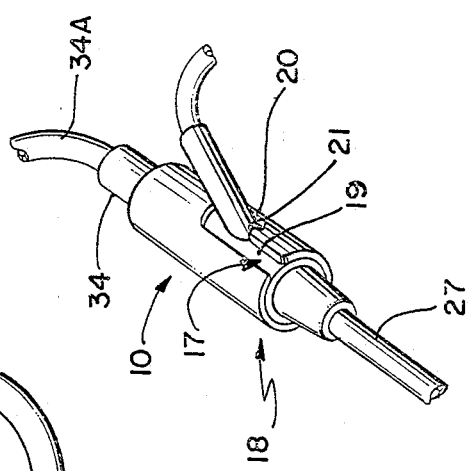
FIG. 3 is an external side elevation view of the assembled device, after locking.

The assembly of the connector 10, Y-tube 25 and luer lock 34 is shown in FIG. 2, prior to locking. Initially, the connector is fitted over the Y-tube, with the slot 17 passing adjacent the sidearm 31 and along the base 32 where the sidearm and Y-tube are joined. The locking motion only requires the connector to be rotated about one-quarter (¼) turn, i e., about 90°, while the needle hub 13 slightly pressures and deflects the 'piggyback' injection port 29. This locking motion rotates the sidearm 31 into the rounded area 20, after which the connector is released, causing the sidearm to be locked into the notch area 21.

A second embodiment of this invention is shown in FIGS. 5-10 and comprises an integrally molded tubular connector 35 having a distal luer fitting 36 and locking ears 37. A needle hub 38 is formed in the distal end, and a factory mounted needle 39 is positioned centrally in the hub. The tubular body of the connector has an exterior wall 45, and an elongate recess 46 is defined on the wall at the proximal end of the connector. The exterior wall 45 at the proximal end defines a series of ridges 47 which engage with an end mounted cap 48 along grooves 49. The end cap 48 defines an alignment slit 50 which aligns with the elongate recess 46 and the sidearm of the Y-tube when these two components are initially engaged, prior to locking.

In the same manner as shown in the embodiment of FIGS. 1-4, a luer slip or luer lock fitting 55 forms a press fit or a lock with the distal luer fitting 36 of the connector 35. The luer lock fitting 55 is connected to an I.V. supply via a feed line 56.

A Y-tube 60, of the same type as shown in FIGS. 1-4, is connected at its proximal end to a primary line 61 which feeds to a patient. The distal end 62 defines a 'piggyback' injection port 63 which fits into the connector 35. A peripheral, circular ridge 64 is formed on the exterior wall of the Y-tube, and has the same function as circular ridge 30. The Y-tube includes a sidearm 65 joined together at the base 66. Additional medication is fed to a patient via a tube 67 attached to the sidearm.

The assembly of the connector 35, Y-tube 60 and luer slip 55 is shown in FIGS. 6 and 9, prior to locking. Initially, the connector is fitted over the Y-tube, with the elongate recess 46 coinciding with the sidearm 65 at its base 66, and the alignment slit 50 of the end cap 48. When fully inserted, the base of the Y-tube will bottom against the recess 46.

As shown in FIGS. 7 and 10, the assembly can then be locked simply by rotating the end cap 48 so that the slit 60 is out of alignment with the recess and the sidearm 65. A rotation of about one-quarter (¼) turn, i.e., about 90° will effectively lock the components, and a distinct clicking sound can be heard, and is produced by engagement of detents (not shown) which are embossed on the cap, and/or housing.

Thus, both embodiments of this invention provide inexpensive locking devices which can be easily engaged and locked, and also unlocked by a specific manipulation. In both cases, the specific manipulations required to unlock the assembly virtually preclude the assembly from being inadvertantly unlocked, or from being unlocked by random patient movements, or by unlocking due to slippage or misengagement between the components.

We claim:

1. A connector assembly for joining a Y-tube and a luer, the Y-tube including an attached sidearm, the assembly comprising:
   a. a resilient, molded, tubular body providing an elongate sidewall and distal and proximal ports, the luer being connected to the distal port, and to an I.V. source, syringe, and the like, and the Y-tube being connected into the proximal port of the tubular body;
   b. a recessed needle mounted within the distal port of the tubular body in liquid connection with the luer; and,
   c. a cut-out area defined on the sidewall, and extending from the proximal port of the tubular body, the cut-out area including i. an alignment portion along which the tubular body slides as it deformably fits along the Y-tube and engages therewith, and ii. a notch area defined by the cut-out area; whereby, the tubular body and Y-tube are locked together by sliding the Y-tube along the alignment portion, and deforming the sidearm of the Y-tube into the notch area.

2. The connector of claim 1, in which the cut-out area is an alignment slot.

3. The connector of claim 1, in which the cut-out area is an alignment recess.

4. A connector assembly for joining a Y-tube and a luer, the Y-tube including an attached sidearm, the assembly comprising:
   a. a resilient, molded, tubular body providing an elongate sidewall and distal and proximal ports, the luer being connected to the distal port, and to an I.V. source, syringe, and the like, and the Y-tube being connected into the proximal port of the tubular body;
   b. a recessed needle mounted within the distal port of the tubular body in liquid connection with the luer; and,
   c. a cut-out area defined on the sidewall, and extending from the proximal port of the tubular body, the cut-out area including i. an alignment slot along which the tubular body slides as it moves along the base of the Y-tube sidearm when the tubular body and Y-tube are fitted together; and,
   d. a shaped portion being defined on the sidewall adjacent the alignment slot, the shaped portion being adapted to engage and lock with the sidearm of the Y-tube when the tubular body is resiliently deformed and rotated with respect to the Y-tube, and to unlock when the tubular body is resiliently deformed as it is rotated with respect to the Y-tube in a reverse manner, the Y-tube and tubular body then being disengaged by sliding them apart.

5. The connector of claim 4, in which the extension of the cut-out portion is shaped to engage and lock with the sidearm of the Y-tube along the base thereof.

6. The connector of claim 4, assembled with the Y-tube and the luer.

7. The connector of claim 4, assembled with the luer.

8. The connector of claim 4, in which the tubular body is molded from a plastic selected from the group consisting of: polyethylene, polypropylene and polycarbonate resins.

9. The connector of claim 4, assembled with the Y-tube.

10. A connector assembly for joining a Y-tube and a luer, the Y-tube including an attached sidearm, the assembly comprising:
    a. a resilient, molded, tubular body providing an elongate sidewall and distal and proximal ports, the luer being connected to the distal port, and to an I.V. source, syringe, and the like, and the Y-tube being connected into the proximal port of the tubular body;
    b. a recessed needle mounted within the distal port of the tubular body in liquid connection with the luer;

c. a cut-out area defined on the sidewall, and extending from the proximal port of the tubular body, the cut-out area including an alignment recess along which the tubular body slides as it moves therealong, and is resiliently deformed onto the Y-tube sidearm when the tubular body and Y-tube are fitted together; and, d. a locking cap defining a peripheral slot, and being adapted to engage the tubular body and Y-tube, the peripheral slot of the locking cap being aligned with the recess and sidearm at its base when the tubular body and Y-tube are fitted together, the cap being adapted for rotation, thereby moving the slot out of alignment with the recess and sidearm at its base to effect locking the tubular body and Y-tube.

11. The connector of claim 10, in which the locking cap is mounted at the proximal end of the connector for engagement therewith, following locking of the connector and Y-tube.

12. The connector of claim 11, assembled with the Y-tube.

13. The connector of claim 11, assembled with the Y-tube and luer.

14. The connector of claim 11, assembled with the luer.

* * * * *

Notice of Adverse Decisions in Interference

In Interference No. 102,673, involving Patent No. 4,964,855, J. J. Todd, E. F. Robinson, R. O. Bare, CONNECTOR WITH RECESSED NEEDLE FOR Y-TUBE, AND ASSEMBLY, final judgment adverse to the patentees was rendered May 12, 1992, as to claims 1-14.

*(Official Gazette August 25, 1992.)*